US009622967B2

(12) United States Patent
Spireas et al.

(10) Patent No.: US 9,622,967 B2
(45) Date of Patent: Apr. 18, 2017

(54) HIGHLY STABLE COMPOSITIONS OF ORALLY ACTIVE NUCLEOTIDE ANALOGUES OR ORALLY ACTIVE NUCLEOTIDE ANALOGUE PRODRUGS

(75) Inventors: Spiridon Spireas, New Hope, PA (US); Ishari Piya, Lansdale, PA (US); Rakesh Grover, Princeton, NJ (US); Sunil Sagi, Fountainville, PA (US); Ram K. Kallur, Fountainville, PA (US)

(73) Assignee: Sigmapharm Laboratories, LLC, Bensalem, PA (US)

( * ) Notice: Subject to any disclaimer, the term of this patent is extended or adjusted under 35 U.S.C. 154(b) by 295 days.

(21) Appl. No.: 13/316,313

(22) Filed: Dec. 9, 2011

(65) Prior Publication Data

US 2012/0196834 A1 Aug. 2, 2012

Related U.S. Application Data

(60) Provisional application No. 61/421,873, filed on Dec. 10, 2010.

(51) Int. Cl.
*A61K 31/675* (2006.01)
*A61K 9/00* (2006.01)
*A61K 9/14* (2006.01)
*A61K 9/20* (2006.01)

(52) U.S. Cl.
CPC ............ *A61K 9/0095* (2013.01); *A61K 9/146* (2013.01); *A61K 9/2027* (2013.01); *A61K 31/675* (2013.01)

(58) Field of Classification Search
None
See application file for complete search history.

(56) References Cited

U.S. PATENT DOCUMENTS

| | | |
|---|---|---|
| 3,929,840 A | 12/1975 | Christensen et al. |
| 4,230,708 A | 10/1980 | De Clercq et al. |
| 4,287,188 A | 9/1981 | Schaeffer |
| 4,347,360 A | 8/1982 | Ogilvie |
| 4,590,269 A | 5/1986 | Prisbe et al. |
| 4,605,658 A | 8/1986 | Holy et al. |
| 4,659,825 A | 4/1987 | Holy et al. |
| 4,670,424 A | 6/1987 | MacCoss et al. |
| 4,724,233 A | 2/1988 | De Clercq et al. |
| 4,808,716 A | 2/1989 | Holy et al. |
| 4,816,447 A | 3/1989 | Ashton et al. |
| 4,816,570 A | 3/1989 | Farquhar |
| 4,952,740 A | 8/1990 | Juge et al. |
| 4,968,788 A | 11/1990 | Farquhar |
| 5,055,458 A | 10/1991 | Bailey et al. |
| 5,130,427 A | 7/1992 | Alexander et al. |
| 5,142,051 A | 8/1992 | Holy et al. |
| 5,302,585 A | 4/1994 | Yu et al. |
| 5,413,996 A | 5/1995 | Bodor |
| 5,470,857 A | 11/1995 | Borcherding et al. |
| 5,476,938 A | 12/1995 | Vemishetti et al. |
| 5,514,798 A | 5/1996 | Bischofberger et al. |
| 5,650,510 A | 7/1997 | Webb, II et al. |
| 5,656,745 A | 8/1997 | Bischofberger et al. |
| 5,659,023 A | 8/1997 | Alexander et al. |
| 5,663,159 A | 9/1997 | Starrett, Jr. et al. |
| 5,686,629 A | 11/1997 | Bischofberger et al. |
| 5,693,798 A | 12/1997 | Kim et al. |
| 5,717,095 A | 2/1998 | Arimilli et al. |
| 5,756,486 A | 5/1998 | Alexander et al. |
| 5,763,424 A | 6/1998 | Yuan |
| 5,792,756 A | 8/1998 | Starrett, Jr. et al. |
| 5,798,340 A | 8/1998 | Bischofberger et al. |
| 5,817,647 A | 10/1998 | Casara et al. |
| 5,837,871 A | 11/1998 | Kim et al. |
| 5,877,166 A | 3/1999 | Reist et al. |

(Continued)

FOREIGN PATENT DOCUMENTS

| | | |
|---|---|---|
| CN | 1698623 A | 11/2005 |
| EP | 0 206 459 A2 | 12/1986 |

(Continued)

OTHER PUBLICATIONS

Li et al., Prodrugs of Nucleoside Analogues for Improved Oral Absorption and Tissue Targeting, Journal of Pharmaceutical Sciences, 97(3), 1109-1134, 2008.*
Janssens et al. "Review: physical chemistry of solid dispersions", Journal of Pharmacy and Pharmacology 2009 (61) 1571-1586.*
Davis et al. "Amorphous solid dispersions of BCS class II drugs: A rational approach to solvent and polymerselection", Chemical Engineering Research and Design 2016 (110) 192-199.*
Chinese Intellectual Property Office, Office Action in Chinese Patent Application No. 201180059661.6, Jun. 16, 2014, 13 pp.

(Continued)

*Primary Examiner* — Jeffrey S Lundgren
*Assistant Examiner* — Michael Schmitt
(74) *Attorney, Agent, or Firm* — Leydig, Voit & Mayer, Ltd.

(57) ABSTRACT

Disclosed are highly stable compositions having outstanding storage stability and/or demonstrating exceptional resistance to aqueous solution degradation, the composition including an orally active nucleotide analog or an orally active nucleotide analog prodrug, which is orally bioavailable, such as adefovir dipivoxil and tenofovir disoproxil. For example, when a composition of the invention is stored for 1 month or for 18 months at 25° C. and 60% relative humidity, its orally active nucleotide analog or orally active nucleotide analog prodrug degrades to provide a composition containing no more than 0.2% or no more than 0.7% by weight of a less orally bioavailable impurity, respectively. Also disclosed are a container/closure package system including the composition and a package insert and methods of manufacturing the composition and treating a patient for a disease or condition, for example, a viral disease or cancer, with the use of the composition.

46 Claims, No Drawings

(56) References Cited

U.S. PATENT DOCUMENTS

| | | | |
|---|---|---|---|
| 5,886,179 | A | 3/1999 | Arimilli et al. |
| 5,922,695 | A | 7/1999 | Arimilli et al. |
| 5,935,946 | A | 8/1999 | Munger, Jr. et al. |
| 5,977,061 | A | 11/1999 | Holy et al. |
| 5,977,089 | A | 11/1999 | Arimilli et al. |
| 6,037,335 | A | 3/2000 | Takashima et al. |
| 6,043,230 | A | 3/2000 | Arimilli et al. |
| 6,057,305 | A | 5/2000 | Holy et al. |
| 6,060,463 | A | 5/2000 | Freeman |
| 6,069,249 | A | 5/2000 | Arimilli et al. |
| 6,225,460 | B1 | 5/2001 | Bischofberger et al. |
| 6,312,662 | B1 | 11/2001 | Erion et al. |
| 6,432,631 | B1 | 8/2002 | Cihlar |
| 6,451,340 | B1 * | 9/2002 | Arimilli et al. ............... 424/464 |
| 6,465,649 | B1 | 10/2002 | Gutierrez et al. |
| 6,635,278 | B1 | 10/2003 | Dahl et al. |
| 6,653,296 | B1 | 11/2003 | Holy et al. |
| 6,727,059 | B1 | 4/2004 | Derrien et al. |
| 6,946,115 | B2 | 9/2005 | Erion et al. |
| 7,115,592 | B2 | 10/2006 | Balzarini et al. |
| 7,157,448 | B2 | 1/2007 | Choi et al. |
| 7,214,668 | B2 | 5/2007 | Reddy et al. |
| 7,351,399 | B2 | 4/2008 | Erion et al. |
| 7,390,791 | B2 | 6/2008 | Becker et al. |
| 7,439,350 | B2 | 10/2008 | Bischofberger et al. |
| 7,572,800 | B2 | 8/2009 | Furman et al. |
| 7,803,788 | B2 | 9/2010 | Becker et al. |
| 7,816,345 | B2 | 10/2010 | Erion et al. |
| 2008/0167325 | A1 * | 7/2008 | Bs et al. .................... 514/263.3 |
| 2011/0201575 | A1 | 8/2011 | Lee et al. |

FOREIGN PATENT DOCUMENTS

| | | |
|---|---|---|
| EP | 0 253 412 A2 | 1/1988 |
| EP | 0 269 947 A1 | 6/1988 |
| EP | 2332941 A2 | 6/2011 |
| WO | WO 2010/032958 A2 | 3/2010 |

OTHER PUBLICATIONS

New Zealand Intellectual Property Office, Office Action in New Zealand Patent Application No. 611438, Nov. 20, 2013, 3 pp.

Mbah, Chika J., "Evaluation of N-Hydroxymethyl Chlorphensin Carbamate and Ethionamide as Potential Prodrugs," Department of Pharmaceutical Chemistry, University of Nigeria, pp. 1-69 (Oct. 1986).

Balzarini, Jan, et al., "Marked in vivo antiretrovirus activity of 9-(2-phosphonylmethoxy-ethyl)adenine, a selective anti-human immunodeficiency virus agent—(acquired immunodeficiency syndrome/antiviral chemotherapy)," *Proc. Natl. Acad. Sci. USA*, vol. 86, pp. 332-336 (Jan. 1989).

Leibman, Kenneth C., et al., "The Metabolism of $P^{82}$-Labeled Ribonucleotides in Tissue Slices and Cell Suspensions," *J. Biol. Chem.*, vol. 216, pp. 823-830 (Feb. 1955).

Roll, Paul M., et al., "The Utilization of Nucleotides by the Mammal—IV. Triply Labeled Purine Nucleotides," *J. Biol. Chem.*, vol. 220, pp. 439-454 (Sep. 1955).

Srivastva, Devendra N., et al., "Bioreversible Phosphate Protective Groups: Synthesis and Stability of Model Acyloxymethyl Phosphates," *Bioorganic Chemistry*, vol. 12, pp. 118-129 (1984).

Cundy, Kenneth C., et al., "Oral Bioavailability of the Antiretroviral Agent 9-(2-phosphonylmethoxyethyl)adenine (PMEA) from Three Formulations of the Prodrug Bis(pivaloyloxymethyl)—PMEA in Fasted Male Cynomolgus Monkeys," *Pharmaceutical Research*, vol. 11, No. 6, pp. 839-843 (Jun. 1994).

Starrett, Jr., John E., et al., "Synthesis and in vitro evaluation of a phosphonate prodrug: bis(pivaloyloxymethyl) 9-(2-phosphonylmethoxyethyl)adenine," *Antiviral Research*, vol. 19, No. 3, pp. 267-273 (Sep. 1992).

Stella, Valentino J., et al., "Prodrugs and Site-Specific Drug Delivery," *Journal of Medicinal Chemistry*, vol. 23, No. 12, pp. 1275-1282 (Dec. 1980).

Farquhar, David, et al., "Biologically Reversible Phosphate-Protective Groups," *Journal of Pharmaceutical Sciences*, vol. 72, No. 3, pp. 324-325 (Mar. 1983).

Anderson, Janet A., et al., "Site of ocular hydrolysis of a prodrug, dipivefrin, and a comparison of its ocular metabolism with that of the parent compound, epinephrine," *Investigative Ophthalmology & Visual Science*, vol. 19, pp. 817-823 (Dec. 1980).

De Clercq, Erik, et al., "Antiviral activity of phosphonylmethoxyalkyl derivatives of purine and pyrimidines," *Antiviral Research*, vol. 8, Nos. 5, 6, pp. 261-272 (Dec. 1987).

Lin, Jung-Chung, et al., "Novel Acyclic Adenosine Analogs Inhibit Epstein-Barr Virus Replication," *Antimicrobial Agents and Chemotherapy*, vol. 31, No. 9, pp. 1431-1433 (Sep. 1987).

Koup, Jeffrey R., et al., "Pharmacokinetics of Cefetamet (Ro 15/8074) and Cefetamet Pivoxil (Ro 15-8075) after Intravenous and Oral Doses in Humans," *Antimicrobial Agents and Chemotherapy*, vol. 32, No. 4, pp. 573-579 (Apr. 1988).

European Patent Office, International Search Report in International Patent Application No. PCT/US2011/064263, Mar. 20, 2014, 4 pp.

European Patent Office, Written Opinion in International Patent Application No. PCT/US2011/064263, Jun. 10, 2013, 6 pp.

\* cited by examiner

HIGHLY STABLE COMPOSITIONS OF ORALLY ACTIVE NUCLEOTIDE ANALOGUES OR ORALLY ACTIVE NUCLEOTIDE ANALOGUE PRODRUGS

CROSS-REFERENCE TO A RELATED APPLICATION

This application claims the benefit of U.S. Provisional Patent Application No. 61/421,873, filed Dec. 10, 2010, the disclosure of which is incorporated by reference.

BACKGROUND OF THE INVENTION

The following description of the background of this invention is provided only to aid in understanding the invention, but is not admitted to be, or to describe, prior art to the invention.

Nucleotide analogues and prodrugs thereof have been extensively studied and described in the literature as potent antiviral and antitumor agents. In particular, various types, forms, uses, compositions, synthetic and analytical methods, drug delivery and other properties of nucleotide or nucleoside analogues including phosphonate nucleotide analogues and their orally active prodrugs, have been disclosed over the last 50 years in a plurality of scientific articles and patents such as, for example, U.S. Pat. No. 7,816,345 to Erion, et al. (Oct. 19, 2010); U.S. Pat. No. 7,803,788 to Becker, et al. (Sep. 28, 2010); U.S. Pat. No. 7,572,800 to Furman, et al. (Aug. 11, 2009); U.S. Pat. No. 7,439,350 to Bischofberger, et al. (Oct. 21, 2008); U.S. Pat. No. 7,390,791 to Becker, et al. (Jun. 24, 2008); U.S. Pat. No. 7,351,399 to Erion, et al. (Apr. 1, 2008); U.S. Pat. No. 7,214,668 to Reddy, et al. (May 8, 2007); U.S. Pat. No. 7,157,448 to Choi, et al. (Jan. 2, 2007); U.S. Pat. No. 7,115,592 to Balzarini, et al. (Oct. 3, 2006); U.S. Pat. No. 6,946,115 to Erion, et al. (Sep. 20, 2005); U.S. Pat. No. 6,727,059 to Derrien, et al. (Apr. 27, 2004); U.S. Pat. No. 6,653,296 to Holy, et al. (Nov. 25, 2003); U.S. Pat. No. 6,635,278 to Dahl, et al. (Oct. 21, 2003); U.S. Pat. No. 6,465,649 to Gutierrez, et al. (Oct. 15, 2002); U.S. Pat. No. 6,451,340 to Arimilli, et al. (Sep. 17, 2002); U.S. Pat. No. 6,432,631 to Cihlar (Aug. 13, 2002); U.S. Pat. No. 6,312,662 to Erion, et al. (Nov. 6, 2001); U.S. Pat. No. 6,225,460 to Bischofberger, et al. (May 1, 2001); U.S. Pat. No. 6,069,249 to Arimilli, et al. (May 30, 2000); U.S. Pat. No. 6,060,463 to Freeman (May 9, 2000); U.S. Pat. No. 6,057,305 to Holy, et al. (May 2, 2000); U.S. Pat. No. 6,043,230 to Arimilli, et al. (Mar. 28, 2000); U.S. Pat. No. 6,037,335 to Takashima, et al. (Mar. 14, 2000); U.S. Pat. No. 5,977,089 to Arimilli, et al. (Nov. 2, 1999); U.S. Pat. No. 5,977,061 to Holy, et al. (Nov. 2, 1999); U.S. Pat. No. 5,935,946 to Munger, Jr., et al. (Aug. 10, 1999); U.S. Pat. No. 5,922,695 to Arimilli, et al. (Jul. 13, 1999); U.S. Pat. No. 5,886,179 to Arimilli, et al. (Mar. 23, 1999); U.S. Pat. No. 5,877,166 to Reist, et al. (Mar. 2, 1999); U.S. Pat. No. 5,837,871 to Kim, et al. (Nov. 17, 1998); U.S. Pat. No. 5,817,647 to Casara, et al. (Oct. 6, 1998); U.S. Pat. No. 5,798,340 to Bischofberger, et al. (Aug. 25, 1998); U.S. Pat. No. 5,792,756 to Starrett, Jr., et al. (Aug. 11, 1998); U.S. Pat. No. 5,763,424 to Yuan (Jun. 9, 1998); U.S. Pat. No. 5,756,486 to Alexander, et al. (May 26, 1998); U.S. Pat. No. 5,717,095 to Arimilli, et al. (Feb. 10, 1998); U.S. Pat. No. 5,693,798 to Kim, et al. (Dec. 2, 1997); U.S. Pat. No. 5,686,629 to Bischofberger, et al. (Nov. 11, 1997); U.S. Pat. No. 5,663,159 to Starrett, Jr., et al. (Sep. 2, 1997); U.S. Pat. No. 5,659,023 to Alexander, et al. (Aug. 19, 1997); U.S. Pat. No. 5,656,745 to Bischofberger, et al. (Aug. 12, 1997); U.S. Pat. No. 5,650,510 to Webb, II, et al. (Jul. 22, 1997); U.S. Pat. No. 5,514,798 to Bischofberger, et al. (May 7, 1996); U.S. Pat. No. 5,476,938 to Vemishetti, et al. (Dec. 19, 1995); U.S. Pat. No. 5,470,857 to Borcherding, et al. (Nov. 28, 1995); U.S. Pat. No. 5,413,996 to Bodor (May 9, 1995); U.S. Pat. No. 5,302,585 to Yu, et al. (Apr. 12, 1994); U.S. Pat. No. 5,142,051 to Holy, et al. (Aug. 25, 1992); U.S. Pat. No. 5,130,427 to Alexander, et al. (Jul. 14, 1992); U.S. Pat. No. 5,055,458 to Bailey, et al. (Oct. 8, 1991); U.S. Pat. No. 4,968,788 to Farquhar (Nov. 6, 1990); U.S. Pat. No. 4,952,740 to Juge, et al. (Aug. 28, 1990); U.S. Pat. No. 4,816,570 to Farquhar (Mar. 28, 1989); U.S. Pat. No. 4,816,447 to Ashton, et al. (Mar. 28, 1989); U.S. Pat. No. 4,808,716 to Holy, et al. (Feb. 28, 1989); U.S. Pat. No. 4,724,233 to De Clercq, et al. (Feb. 9, 1988); U.S. Pat. No. 4,670,424 to MacCoss, et al. (Jun. 2, 1987); U.S. Pat. No. 4,659,825 to Holy, et al. (Apr. 21, 1987); U.S. Pat. No. 4,605,658 to Holy, et al. (Aug. 12, 1986); U.S. Pat. No. 4,590,269 to Prisbe, et al. (May 20, 1986); U.S. Pat. No. 4,347,360 to Ogilvie (Aug. 31, 1982); U.S. Pat. No. 4,287,188 to Schaeffer (Sep. 1, 1981); U.S. Pat. No. 4,230,708 to De Clercq, et al. (Oct. 28, 1980); and U.S. Pat. No. 3,929,840 to Christensen, et al. (Dec. 30, 1975). The above patents also include lists of many different references such as scientific papers, reviews and presentations relevant to nucleotide analogues. Such scientific articles along with the patents listed above are expressly incorporated herein by reference in their entirety.

Undoubtedly, regarding their antiviral activity against a broad spectrum of DNA and RNA viruses, one of the most important classes of known nucleotide analogues encountered in the literature is that of the phosphonate nucleotide analogues, especially that of the methoxy-phosphonate nucleotide analogues such as phosphinyl-methoxy-ethyl-adenine (i.e., PMEA or adefovir) and phosphinyl-methoxy-propyl-adenine (i.e., PMPA or tenofovir). However, due to their increased polarity attributed to the negative charges of the phosphorus atom, these compounds cannot be effective orally since they cannot efficiently penetrate the lipophilic membranes of the gastrointestinal tract and cells of various tissues. To address this problem, several investigators have reported prodrugs or intermediates of said compounds which use biologically reversible groups which are attached to these compounds via ether, ester, carbonate, amide or other types of physiologically hydrolysable bonds, thereby masking the polarity of the original entity and making it orally active since said protective groups can initially traverse the cell membranes and subsequently detach in physiologic conditions to reintroduce to the target cells the original effective medicament.

For example, certain prodrug diesters of PMEA and PMPA, such as 9-[2-[bis[(pivaloyloxy)-methoxy]phosphinyl]methoxy]ethyl]adenine, i.e., bis(POM)PMEA or adefovir dipivoxil, and 9-[(R)-2-[[bis[[(isopropoxycarbonyl)oxy]methoxy]phosphinyl]-methoxy]propyl]adenine, i.e., bis (POC)PMPA or tenofovir disoproxil, have been reported to exhibit significantly increased oral bioavailability as compared to their original compounds. In fact, Starrett, Jr., et al. in U.S. Pat. No. 5,663,159 report that the relative oral bioavailability (as compared to the corresponding absolute intravenous bioavailability) of adefovir is only 7.8 whereas that of its diesterified prodrug, adefovir dipivoxil, was found to be more than double, i.e., 17.0. Similarly, tenofovir disoproxil, the diesterified prodrug form of tenofovir, is significantly more bioavailable orally than the original drug, tenofovir. On the other hand, the monoesters of both adefovir and tenofovir, i.e., mono(POM)PMEA and mono(POC) PMPA, respectively, have been found to be significantly less orally bioavailable even as compared to their original, non-derivatized compounds. In fact, U.S. Pat. No. 5,663,159 discloses that the relative oral bioavailability of the monoester of adefovir is only 6.5, which is even less than that of the original compound adefovir (7.8) and, of course, that of its diester adefovir dipivoxil (17.0).

A constant and rather important drawback of the prodrug approach, however, has been the significant instability of the prepared prodrugs which tend to hydrolyze their ester linkages during synthesis, manufacturing and on storage, either stored by themselves or in pharmaceutical product formulations, thereby losing their protective masking groups and, consequently, exhibiting significantly reduced oral activity. To address this drawback, attempts have been made to introduce various types of crystal forms of such prodrugs in order to obtain reduced impurity levels during their synthesis and manufacturing and to improve the storage stability of the prepared prodrugs and their pharmaceutical compositions.

Arimilli, et al. in U.S. Pat. No. 6,451,340 disclose crystalline forms of adefovir dipivoxil in pharmaceutical compositions which, according to the inventors, are more manufacturable and stable than previous forms, e.g., the amorphous form, of the same drug. Using an ordinary composition of these adefovir dipivoxil crystals with other inactive ingredients, the assignee of the '340 patent, Gilead Sciences, Inc., has obtained an NDA approval for HEPSERA® (adefovir dipivoxil) tablets, 10 mg with an NDA application number of N021449. When HEPSERA® tablets were stored at a temperature of 60° C. and 75% relative humidity ("RH"), about 3.1% w/w of the less orally bioavailable monoester, mono(POM)PMEA, was formed in 5 days with respect to the original 10 mg quantity of the more bioavailable diester, adefovir dipivoxil, present initially in each HEPSERA® tablet. Furthermore, when the product of NDA #N021449 was stored at 40° C. and 75% RH, about 1.94%, 2.16% and 2.61% w/w of the less bioavailable monoester was formed in 1, 2 and 3 months, respectively.

Dahl, et al. in U.S. Pat. No. 6,635,278 assigned to the makers of HEPSERA® Tablets, Gilead Sciences, Inc., disclose the addition of an alkaline excipient such as magnesium or calcium carbonate to tablet compositions comprising crystalline adefovir dipivoxil and also containing optionally L-carnitine-L-tartrate. After storing these compositions for 6 to 8 days at 60° C. and 30% RH, the less bioavailable monoester was formed in weight percentages ranging from 2.8% to 4.4%. Furthermore, depending on the amount of desiccant included in the packaging of the prepared tablets, 96.6% to 97.3% w/w of adefovir dipivoxil remained in the tested preferred tablet compositions (i.e., 2.7% to 3.4% w/w degradation) after storage at 60° C. and 75% RH for 1 week, whereas 97.6% and 97.8% w/w of the drug remained in the most preferred composition (i.e., 2.2% and 2.4% w/w degradation) after storage at 40° C. and 75% RH for 3 months.

In addition, Munger, Jr., et al. in U.S. Pat. No. 5,935,946 also assigned to Gilead Sciences, Inc., disclose a crystalline form of the diester bis(POC)PMPA (or tenofovir disoproxil) in which the crystals are made of tenofovir disoproxil fumarate complexes each comprising one part of tenofovir disoproxil and one part of fumaric acid. The disclosed crystals are claimed not only to increase the stability as compared to the original diester prodrug, tenofovir disoproxil, but also, as compared to another crystalline salt, namely, tenofovir disoproxil citrate. After storing the materials for 3 days at 60° C. and 75% RH, the less bioavailable monoester, mono(POC)—PMPA, was formed in weight percentages of 3.1% and 58.9% from the tenofovir disoproxil fumarate and citrate crystals, respectively. On the other hand, storage of the materials at 40° C. and 75% RH resulted in formation of 1.9% and 2.9% of the less bioavailable monoester in 1 and 2 months, respectively, from the tenofovir disoproxil fumarate material, whereas 7.1% and 22.4% w/w of the monoester was formed in 1 and 2 months, respectively, from the tenofovir disoproxil citrate material. It should be also mentioned that during the preparation of these crystalline materials, it is reported that 1% of the undesirable and less bioavailable monoester had been already formed soon after production of both of these materials.

Another possible disadvantage of the prodrug approach could also be a rather high rate of degradation and chemical instability of prepared prodrugs when exposed to aqueous environments, namely, prodrugs suspended or dissolved in gastric or intestinal fluids or absorbed in the blood at a molecular state. Depending on the synthesis of the prodrug and/or the manufacturing or storage of the prodrug, or of the finished product containing such prodrug, its particular or molecular dispersions in aqueous environments may exhibit unacceptably fast drug destabilization rates resulting most probably from the hydrolysis of their ester linkages, thereby possibly leading to high levels of orally inactive degradation products or other impurities of such prodrug. In fact, based on recent studies conducted by the inventors named in the present application, it was found that the crystalline form of Adefovir Dipivoxil contained in the commercial brand product HEPSERA® hydrolyzes in-situ to as much as 11.6% by weight of its significantly less orally bioavailable monoester form when a HEPSERA® 10 mg tablet is dissolved in 250 milliliters of purified water maintained at 37° C. and stirred at 60 rpm for one hour. To date, no significant attempts have been made to address this type of in-situ aqueous solution degradation of such prodrugs.

In view of the foregoing, existing methods, forms and compositions of orally active nucleotide analogue prodrugs do not yield products: (i) containing insignificant amounts of undesirable and less orally bioavailable impurities, (ii) exhibiting high storage stability whether stored alone, in combination or as finished products, and (iii) demonstrating reduced in-situ degradation while being suspended or dissolved in aqueous environments. As discussed, it appears that the available/disclosed past and present forms and compositions of such orally active prodrugs of nucleotide analogues, in their so far best performance mode, degrade to yield more than 2.2% w/w of their significantly less orally bioavailable impurity after storage at 40° C. and 75% RH for 3 months. In fact, based on this quite pronounced destabilization potential of such analogue prodrugs, it is highly possible that there might have been instances wherein promising orally active nucleotide analogue prodrugs have been rejected from clinical trials due to their manufacturing and storage instability resulting from inadequate stabilization techniques.

The foregoing shows that there exists an unmet need to form compositions of orally active nucleotide analogues and orally active nucleotide analogue prodrugs, which would not only present high stability properties during their storage by degrading to significantly reduced amounts of their less orally bioavailable impurities as compared to current forms and compositions, but also, would yield significantly lower initial quantities of such undesirable impurities soon after their manufacturing, and furthermore, would minimally degrade in-situ to their less orally bioavailable impurities when suspended or dissolved in aqueous environments such as blood and gastrointestinal fluids.

BRIEF SUMMARY OF THE INVENTION

The invention provides highly stable forms, compositions and pharmaceutical products of orally active nucleotide analogues and orally active nucleotide analogue prodrugs possessing outstanding storage stability properties at various temperature and humidity conditions and exceptional resistance to in-situ aqueous solution degradation, by decomposing to significantly reduced amounts of their less orally bioavailable impurities as compared to current existing forms, compositions and pharmaceutical products of such orally active nucleotide analogues and orally active nucleotide analogue prodrugs.

Accordingly, the invention provides a composition comprising, consisting essentially of, or consisting of, an orally active nucleotide analogue or an orally active nucleotide analogue prodrug, which is orally bioavailable, and a pharmaceutically acceptable and inactive polymer that stabilizes the orally active nucleotide analogue or the orally active nucleotide analogue prodrug against degradation, wherein the nucleotide analogue or nucleotide analogue prodrug degrades to provide a composition containing no more than (a) 0.8% by weight of a less bioavailable impurity, relative to the original amount of the orally active nucleotide analogue or the orally active nucleotide analogue prodrug, when the composition is maintained at a temperature of 25° C. and at 60% RH for a period of 1 month; (b) 1.2% by weight of a less bioavailable impurity, relative to the original amount of the orally active nucleotide analogue or the orally active nucleotide analogue prodrug, when the composition is maintained at a temperature of 25° C. and at 60% RH for a period of 12 months; (c) 1.5% by weight of a less bioavailable impurity, relative to the original amount of the orally active nucleotide analogue or the orally active nucleotide analogue prodrug, when the composition is maintained at a temperature of 25° C. and at 60% RH for a period of 24 months; (d) 2.0% by weight of a less bioavailable impurity, relative to the original amount of the orally active nucleotide analogue or the orally active nucleotide analogue prodrug, when the composition is maintained at a temperature of 40° C. and at a relative humidity of 75% for a period of 3 months; (e) 1.75% by weight of a less bioavailable impurity, relative to the original amount of the orally active nucleotide analogue or the orally active nucleotide analogue prodrug, when the composition is maintained at a temperature of 40° C. and at 75% RH for a period of 2 months; (f) 1.5% by weight of a less bioavailable impurity, relative to the original amount of the orally active nucleotide analogue or the orally active nucleotide analogue prodrug, when the composition is maintained at a temperature of 40° C. and at 75% RH for a period of 1 month; and/or (g) 2.5% by weight of a less bioavailable impurity, relative to the original amount of the orally active nucleotide analogue or the orally active nucleotide analogue prodrug, when the composition is maintained at a temperature of 60° C. and at 75% RH for a period of 5 days; wherein said less bioavailable impurity has at least 10% less oral bioavailability than the orally active nucleotide analogue or the orally active nucleotide analogue prodrug.

The invention also provides a composition comprising, consisting essentially of, or consisting of an orally active nucleotide analogue or an orally active nucleotide analogue prodrug, which is orally bioavailable, and a pharmaceutically acceptable and inactive polymer that stabilizes the orally active nucleotide analogue or the orally active nucleotide analogue prodrug against degradation, wherein, when a unit dose of such composition containing 10 mg of the orally active nucleotide analogue or the orally active nucleotide analogue prodrug is dissolved in purified water maintained at 37° C., said orally active nucleotide analogue or orally active nucleotide analogue prodrug degrades to provide a solution containing no more than (a) 10.5% by weight of a less bioavailable impurity, relative to the original amount of the orally active nucleotide analogue or the orally active nucleotide analogue prodrug, when said unit dose of the composition is dissolved in 250 milliliters of said purified water stirred at 60 rpm by a magnetic stirrer for a period of 1 hour; (b) 6.5% by weight of a less bioavailable impurity, relative to the original amount of the orally active nucleotide analogue or the orally active nucleotide analogue prodrug, when said unit dose of the composition is dissolved in 250 milliliters of said purified water stirred at 60 rpm by a magnetic stirrer for a period of 30 minutes; (c) 6.4% by weight of a less bioavailable impurity, relative to the original amount of the orally active nucleotide analogue or the orally active nucleotide analogue prodrug, when said unit dose of the composition is dissolved in 500 milliliters of said purified water stirred at 50 rpm by a dissolution paddle for a period of 2 hours; (d) 4.2% by weight of a less bioavailable impurity, relative to the original amount of the orally active nucleotide analogue or the orally active nucleotide analogue prodrug, when said unit dose of the composition is dissolved in 500 milliliters of said purified water stirred at 50 rpm by a dissolution paddle for a period of 1 hour; and/or (e) 3.0% by weight of a less bioavailable impurity, relative to the original amount of the orally active nucleotide analogue or the orally active nucleotide analogue prodrug, when said unit dose of the composition is dissolved in 500 milliliters of said purified water stirred at 50 rpm by a dissolution paddle for a period of 30 minutes; wherein said less bioavailable impurity has at least 10% less oral bioavailability than the orally active nucleotide analogue or the orally active nucleotide analogue prodrug.

The invention also provides methods of manufacture of such compositions and products of highly stable pharmaceutical formulations comprising stable forms and compositions of orally active nucleotide analogues or of orally active nucleotide analogue prodrugs, exemplified by adefovir dipivoxil ("AD"), the orally bioavailable diester prodrug of the methoxyphosphonate nucleotide analogue, adefovir.

Embodiments of the invention include highly stable forms, including amorphous forms, and compositions, including polymeric solid solutions, of orally active nucleotide analogue prodrugs, exemplified by AD.

Other embodiments include highly stable amorphous forms of AD and solid solutions of AD with polymers such as copovidone prepared by using certain preferred organic solvents such as acetone to dissolve the AD and the polymers and then rapidly evaporating the certain preferred solvent to produce the stable composition of the AD/polymer solid solution.

Other embodiments include stable pharmaceutical formulations, compositions, and/or products of AD comprising, consisting essentially of, or consisting of, stable amorphous forms and/or AD compositions such as AD/polymer solid solutions, and at least one pharmaceutically acceptable inactive ingredient.

Other embodiments include stable intermediate compositions of orally active nucleotide analogue prodrugs exemplified by AD, containing AD in various forms including amorphous AD and AD formulations in the form of unit dosages, such as tablets or capsules comprising about 0.1%-

99.9% w/w AD and about 0.1%-99.9% w/w of a polymer, and typically comprising about 2 to 98% w/w AD and about 98-2% w/w of a polymer.

Other embodiments include a product produced by the process of contacting a solution of an orally active nucleotide analogue or nucleotide analogue prodrug exemplified by AD with a polymer such as copovidone, or by preparing a solution of the nucleotide analogue prodrug and the polymer.

Other embodiments include the methods to produce the aforementioned highly stable pharmaceutical products, formulations, compositions, forms and solutions of orally active nucleotide analogue prodrugs exemplified by AD.

Additional embodiments of the invention include treating a mammal, e.g., a patient, with a stable product, composition or form of an orally active nucleotide analogue prodrug exemplified by AD, which when administered orally to such mammal will provide or promote a therapeutic effect for a certain illness.

Further embodiments of the invention provide packages containing highly stable pharmaceutical products of orally active nucleotide analogues or orally active nucleotide analogue prodrugs exemplified by AD, which are accompanied by printed materials informing patients and medical care workers that the contained products have exceptional drug purity and resistance to drug destabilization or degradation since their drug contents degrade to no more than 1.5% w/w, or preferably no more than 1.0% w/w, of their less bioavailable impurities for the shelf-life of the products, and that such high purity and resistance to destabilization are desired to achieve the best therapeutic mode, including optimum safety and efficacy, intended for such packaged pharmaceutical products of the orally active nucleotide analogues or the orally active nucleotide analogue prodrugs.

Further embodiments of the invention also provide packages containing highly stable pharmaceutical products of orally active nucleotide analogues or orally active nucleotide analogue prodrugs exemplified by AD, which are accompanied by printed materials informing patients and medical care workers that the contained products have exceptional resistance to in-situ drug degradation in aqueous environments such as blood and gastrointestinal fluids, since their drug contents degrade minimally to their less bioavailable impurities when such contained products are being dissolved or absorbed in such aqueous environments, and that such exceptional resistance to in-situ aqueous solution degradation is, desired to achieve the best therapeutic mode, including optimum safety and efficacy, intended for such packaged pharmaceutical products of the orally active nucleotide analogues or the orally active nucleotide analogue prodrugs.

DETAILED DESCRIPTION OF THE INVENTION

In accordance with an embodiment, the invention provides a composition comprising an orally active nucleotide analogue or an orally active nucleotide analogue prodrug, which is orally bioavailable, and a pharmaceutically acceptable and inactive polymer that stabilizes the orally active nucleotide analogue or the orally active nucleotide analogue prodrug against degradation, wherein the nucleotide analogue or nucleotide analogue prodrug degrades to provide a composition containing no more than (a) 0.8% by weight of a less bioavailable impurity, relative to the original amount of the orally active nucleotide analogue or the orally active nucleotide analogue prodrug, when the composition is maintained at a temperature of 25° C. and at 60% RH for a period of 1 month; (b) 1.2% by weight of a less bioavailable impurity, relative to the original amount of the orally active nucleotide analogue or the orally active nucleotide analogue prodrug, when the composition is maintained at a temperature of 25° C. and at 60% RH for a period of 12 months; (c) 1.5% by weight of a less bioavailable impurity, relative to the original amount of the orally active nucleotide analogue or the orally active nucleotide analogue prodrug, when the composition is maintained at a temperature of 25° C. and at 60% RH for a period of 24 months; (d) 2.0% by weight of a less bioavailable impurity, relative to the original amount of the orally active nucleotide analogue or the orally active nucleotide analogue prodrug, when the composition is maintained at a temperature of 40° C. and at 75% RH for a period of 3 months; (e) 1.75% by weight of a less bioavailable impurity, relative to the original amount of the orally active nucleotide analogue or the orally active nucleotide analogue prodrug, when the composition is maintained at a temperature of 40° C. and at 75% RH for a period of 2 months; (f) 1.5% by weight of a less bioavailable impurity, relative to the original amount of the orally active nucleotide analogue or the orally active nucleotide analogue prodrug, when the composition is maintained at a temperature of 40° C. and at 75% RH for a period of 1 month; and/or (g) 2.5% by weight of a less bioavailable impurity, relative to the original amount of the orally active nucleotide analogue or the orally active nucleotide analogue prodrug, when the composition is maintained at a temperature of 60° C. and at 75% RH for a period of 5 days; wherein said less bioavailable impurity has at least 10% less oral bioavailability than the orally active nucleotide analogue or the orally active nucleotide analogue.

In accordance with another embodiment, the invention provides a composition, comprising an orally active nucleotide analogue or an orally active nucleotide analogue prodrug, which is orally bioavailable, and a pharmaceutically acceptable and inactive polymer that stabilizes the orally active nucleotide analogue or the orally active nucleotide analogue prodrug against degradation, wherein, when a unit dose of such composition containing 10 mg of the orally active nucleotide analogue or the orally active nucleotide analogue prodrug is dissolved in purified water maintained at 37° C., said orally active nucleotide analogue or orally active nucleotide analogue prodrug degrades to provide a solution containing no more than (a) 10.5% by weight of a less bioavailable impurity, relative to the original amount of the orally active nucleotide analogue or the orally active nucleotide analogue prodrug, when said unit dose of the composition is dissolved in 250 milliliters of said purified water stirred at 60 rpm by a magnetic stirrer for a period of 1 hour; (b) 6.5% by weight of a less bioavailable impurity, relative to the original amount of the orally active nucleotide analogue or the orally active nucleotide analogue prodrug, when said unit dose of the composition is dissolved in 250 milliliters of said purified water stirred at 60 rpm by a magnetic stirrer for a period of 30 minutes; (c) 6.4% by weight of a less bioavailable impurity, relative to the original amount of the orally active nucleotide analogue or the orally active nucleotide analogue prodrug, when said unit dose of the composition is dissolved in 500 milliliters of said purified water stirred at 50 rpm by a dissolution paddle for a period of 2 hours; (d) 4.2% by weight of a less bioavailable impurity, relative to the original amount of the orally active nucleotide analogue or the orally active nucleotide analogue prodrug, when said unit dose of the composition is dissolved in 500 milliliters of said purified water stirred at 50 rpm by a dissolution paddle for a period of 1 hour; and/or (e) 3.0% by weight of a less bioavailable impurity, relative to the original amount of the orally active nucleotide analogue or the orally active nucleotide analogue prodrug, when said unit dose of the composition is dissolved in 500 milliliters of said purified water stirred at 50 rpm by a dissolution paddle for a period of 30 minutes; wherein said less bioavailable impurity has at least 10% less oral bioavailability than the orally active nucleotide analogue or the orally active nucleotide analogue.

In accordance with the present invention, an orally active nucleotide analogue or an orally active nucleotide analogue prodrug is a compound that can be absorbed in the body when administered orally in a total amount which represents more than 9% of the total amount of compound (i.e., the nucleotide analogue or nucleotide analogue prodrug) absorbed in the body when the same amount of said compound is administered intravenously to the same patient. Such percent ratio of the total amounts of compound absorbed after oral and intravenous administration of the same dose of said compound to a patient is also known as the relative oral bioavailability of the compound.

In embodiments of the invention, the terms "bioavailability" and/or "oral bioavailability" of an orally active nucleotide analogue drug or an orally active nucleotide analogue prodrug, or a medicinal compound in general, mean the ratio of the Area Under the blood concentration versus time Curve (i.e., "AUC") and the orally administered dose of the corresponding nucleotide analogue drug or nucleotide analogue prodrug, or the medicinal compound in general.

In embodiments of the invention, the "less bioavailable impurity" and/or the "less orally bioavailable impurity" has at least 10%, 12%, 15%, 20%, 25%, 30%, 40%, 50%, 60%, 70%, 80%, or 90% less oral bioavailability than that of its corresponding orally active nucleotide analogue or orally active nucleotide analogue prodrug.

In accordance with the invention, degradation of the orally active nucleotide analogue or the orally active nucleotide analogue prodrug can involve any mechanism by which the oral activity is lost, e.g., loss of one or more of the protective or masking groups, hydrolysis, crystallization, turning into an unstable amorphous form, undergoing crystallographic transformation, formation of solvates or hydrates of varying degrees of solvation or hydration, oxidation, reduction, crosslinking, isomerization, inversion, cyclization, ring opening, and the like.

In accordance with embodiments of the invention, the composition can include any suitable nucleotide analogue or nucleotide analogue prodrug, for example, an antiviral or an antitumor agent. In a particular embodiment, the nucleotide analogue or the nucleotide analogue prodrug is an antiviral agent.

In accordance with an embodiment, the nucleotide analogue prodrug of the composition of the invention, is a phosphonate nucleotide analogue prodrug. Examples of such prodrugs include 9-[2-[bis[(pivaloyloxy)-methoxy] phosphinyl]methoxy]ethyl]adenine (the bis(POM)PMEA diester of adefovir) and 9-[(R)-2-[bis[(isopropoxycarbonyl)-oxymethoxy]-phosphinyl]methoxy]propyl]adenine (the bis (POC)PMPA diester of tenofovir).

In the above embodiment, the less orally bioavailable impurity is 9-[2-(pivaloyloxy)-methoxyphosphinyl] methoxy]ethyl]adenine, 9-[(R)-2-[(isopropoxycarbonyl)-oxy]methoxyphosphinyl]methoxy]propyl]adenine, adefovir, tenofovir, or any combination thereof.

In accordance with the invention, the nucleotide analogue or the nucleotide analogue prodrug can be in a crystalline form or in an amorphous form, particularly in an amorphous form.

In accordance with the invention, the composition comprises at least one pharmaceutically acceptable inactive polymer that stabilizes the orally active nucleotide analogue or the orally active nucleotide analogue prodrug against degradation during manufacturing, storage, and/or when suspended or dissolved in aqueous environments.

In accordance with an embodiment, the composition comprises an amorphous solid solution of an orally active nucleotide analogue or an orally active nucleotide analogue prodrug and a pharmaceutically acceptable inactive polymer. For example, the amorphous solid solution of the orally active nucleotide analogue or the orally active nucleotide analogue prodrug and the pharmaceutically acceptable inactive polymer is a molecular dispersion of adefovir dipivoxil or tenofovir disoproxil and copovidone. The amorphous solid solution can be prepared by dissolving the nucleotide analogue or the orally active nucleotide analogue prodrug and the pharmaceutically acceptable inactive polymer in a liquid organic solvent and evaporating the organic solvent.

In an embodiment, the liquid organic solvent is selected from the group consisting of volatile alcohols, volatile ketones, and volatile halocarbons, and combinations thereof. Examples of organic solvents include methyl alcohol, ethyl alcohol, isopropyl alcohol, acetone, methyl ethyl ketone, methylene chloride, dichloroethanes, and the like.

In accordance with an embodiment, the orally active nucleotide analogue prodrug is adefovir dipivoxil and the liquid organic solvent is acetone.

In accordance with an embodiment, the pharmaceutically acceptable inactive polymer is copovidone, which is a vinylpyrrolidone-vinyl acetate copolymer.

In any of the embodiments, the composition can further include one or more pharmaceutically acceptable inactive ingredients. For example, the pharmaceutically acceptable inactive ingredients are selected from the group consisting of fillers, diluents, binders, disintegrants, glidants, lubricants, and matrix forming materials.

In accordance with an embodiment, the one or more pharmaceutically acceptable inactive ingredients are selected from the group consisting of anhydrous lactose, microcrystalline cellulose, silicon dioxide, and magnesium stearate.

In accordance with the invention, the composition is a solid dosage form, for example, a tablet, a capsule, or a powder.

In accordance with an embodiment, the invention provides a composition comprising an orally active nucleotide analogue or an orally active nucleotide analogue prodrug, which is orally bioavailable, and a pharmaceutically acceptable and inactive polymer that stabilizes the orally active nucleotide analogue or the orally active nucleotide analogue prodrug against degradation, wherein the nucleotide analogue or nucleotide analogue prodrug degrades to provide a composition containing no more than 0.8% by weight of a less bioavailable impurity, preferably no more than 0.6% by weight of a less bioavailable impurity, more preferably no more than 0.4% by weight of a less bioavailable impurity, and even more preferably no more than 0.2% by weight of a less bioavailable impurity, relative to the original amount of the orally active nucleotide analogue or the orally active nucleotide analogue prodrug, when the composition is maintained at a temperature of 25° C. and at 60% RH for a period of 1 month.

In accordance with another embodiment, the invention provides a composition comprising an orally active nucleotide analogue or an orally active nucleotide analogue prodrug, which is orally bioavailable, and a pharmaceutically acceptable and inactive polymer that stabilizes the orally active nucleotide analogue or the orally active nucleotide analogue prodrug against degradation, wherein the nucleotide analogue or nucleotide analogue prodrug degrades to provide a composition containing no more than 1.2% by weight of a less bioavailable impurity, preferably no more than 1.0% by weight of a less bioavailable impurity, more preferably no more than 0.8% by weight of a less bioavailable impurity, and even more preferably no more than 0.6% by weight of a less bioavailable impurity, relative to the original amount of the orally active nucleotide analogue or the orally active nucleotide analogue prodrug, when the composition is maintained at a temperature of 25° C. and at 60% RH for a period of 12 months.

In accordance with another embodiment, the invention provides a composition comprising an orally active nucleotide analogue or an orally active nucleotide analogue prodrug, which is orally bioavailable, and a pharmaceutically acceptable and inactive polymer that stabilizes the orally active nucleotide analogue or the orally active nucleotide analogue prodrug against degradation, wherein the nucleotide analogue or nucleotide analogue prodrug degrades to provide a composition containing no more than 1.5% by weight of a less bioavailable impurity, preferably no more than 1.2% by weight of a less bioavailable impurity, more preferably no more than 1.0% by weight of a less bioavailable impurity, and even more preferably no more than 0.8% by weight of a less bioavailable impurity, relative to the original amount of the orally active nucleotide analogue or the orally active nucleotide analogue prodrug, when the composition is maintained at a temperature of 25° C. and at 60% RH for a period of 24 months.

In accordance with yet another embodiment, the invention provides a composition comprising an orally active nucleotide analogue or an orally active nucleotide analogue prodrug, which is orally bioavailable, and a pharmaceutically acceptable and inactive polymer that stabilizes the orally active nucleotide analogue or the orally active nucleotide analogue prodrug against degradation, wherein the nucleotide analogue or nucleotide analogue prodrug degrades to provide a composition containing no more than 2.0% by weight of a less bioavailable impurity, preferably no more than 1.5% by weight of a less bioavailable impurity, more preferably no more than 1.0% by weight of a less bioavailable impurity, and even more preferably no more than 0.75% by weight of a less bioavailable impurity, relative to the original amount of the orally active nucleotide analogue or the orally active nucleotide analogue prodrug, when the composition is maintained at a temperature of 40° C. and at 75% RH for a period of 3 months.

In accordance with a further embodiment, the invention provides a composition comprising an orally active nucleotide analogue or an orally active nucleotide analogue prodrug, which is orally bioavailable, and a pharmaceutically acceptable and inactive polymer that stabilizes the orally active nucleotide analogue or the orally active nucleotide analogue prodrug against degradation, wherein the nucleotide analogue or nucleotide analogue prodrug degrades to provide a composition containing no more than 1.75% by weight of a less bioavailable impurity, preferably no more than 1.5% by weight of a less bioavailable impurity, more preferably no more than 1.0% by weight of a less bioavailable impurity, and even more preferably no more than 0.6% by weight of a less bioavailable impurity, relative to the original amount of the orally active nucleotide analogue or the orally active nucleotide analogue prodrug, when the composition is maintained at a temperature of 40° C. and at 75% RH for a period of 2 months.

In a further embodiment, the invention provides a composition comprising an orally active nucleotide analogue or an orally active nucleotide analogue prodrug, which is orally bioavailable, and a pharmaceutically acceptable and inactive polymer that stabilizes the orally active nucleotide analogue or the orally active nucleotide analogue prodrug against degradation, wherein the nucleotide analogue or nucleotide analogue prodrug degrades to provide a composition containing no more than 1.5% by weight of a less bioavailable impurity, preferably no more than 1.0% by weight of a less bioavailable impurity, more preferably no more than 0.75% by weight of a less bioavailable impurity, and even more preferably no more than 0.5% by weight of a less bioavailable impurity, relative to the original amount of the orally active nucleotide analogue or the orally active nucleotide analogue prodrug, when the composition is maintained at a temperature of 40° C. and at 75% RH for a period of 1 month.

In a further embodiment, the invention provides a composition comprising an orally active nucleotide analogue or an orally active nucleotide analogue prodrug, which is orally bioavailable, and a pharmaceutically acceptable and inactive polymer that stabilizes the orally active nucleotide analogue or the orally active nucleotide analogue prodrug against degradation, wherein the nucleotide analogue or nucleotide analogue prodrug degrades to provide a composition containing no more than 2.5% by weight of a less bioavailable impurity, preferably no more than 2.0% by weight of a less bioavailable impurity, more preferably no more than 1.5% by weight of a less bioavailable impurity, most preferably no more than 1.0% by weight of a less bioavailable impurity, and even most preferably no more than 0.7% by weight of a less bioavailable impurity, relative to the original amount of the orally active nucleotide analogue or the orally active nucleotide analogue prodrug, when the composition is maintained at a temperature of 60° C. and at 75% RH for a period of 5 days.

In accordance with another embodiment, the invention provides a composition comprising an orally active nucleotide analogue or an orally active nucleotide analogue prodrug, which is orally bioavailable, and a pharmaceutically acceptable and inactive polymer that stabilizes said nucleotide analogue or nucleotide analogue prodrug against degradation, wherein the orally active nucleotide analogue or orally active nucleotide analogue prodrug degrades to provide a solution containing no more than 10.5% by weight of a less bioavailable impurity, preferably no more than 8.5% by weight of a less bioavailable impurity, more preferably no more than 6.0% by weight of a less bioavailable impurity, and even more preferably no more than 4.0% by weight of a less bioavailable impurity, relative to the original amount of the orally active nucleotide analogue or the orally active nucleotide analogue prodrug, when the unit dose of the composition containing 10 mg of said nucleotide analogue or nucleotide analogue prodrug is being dissolved in 250 milliliters of purified water maintained at 37° C. and stirred at 60 rpm by a magnetic stirrer for a period of 1 hour.

In accordance with yet another embodiment, the invention provides a composition comprising an orally active nucleotide analogue or an orally active nucleotide analogue prodrug, which is orally bioavailable, and a pharmaceutically acceptable and inactive polymer that stabilizes said nucleotide analogue or nucleotide analogue prodrug against degradation, wherein the orally active nucleotide analogue or orally active nucleotide analogue prodrug degrades to provide a solution containing no more than 6.5% by weight of a less bioavailable impurity, preferably no more than 5.5% by weight of a less bioavailable impurity, more preferably no more than 4.3% by weight of a less bioavailable impurity, and even more preferably no more than 3.0% by weight of a less bioavailable impurity, relative to the original amount of the orally active nucleotide analogue or the orally active nucleotide analogue prodrug, when the unit dose of the composition containing 10 mg of said nucleotide analogue or nucleotide analogue prodrug is being dissolved in 250 milliliters of purified water maintained at 37° C. and stirred at 60 rpm by a magnetic stirrer for a period of 30 minutes.

In accordance with a further embodiment, the invention provides a composition comprising an orally active nucleotide analogue or an orally active nucleotide analogue prodrug, which is orally bioavailable, and a pharmaceutically acceptable and inactive polymer that stabilizes said nucleotide analogue or nucleotide analogue prodrug against degradation, wherein the orally active nucleotide analogue or orally active nucleotide analogue prodrug degrades to provide a solution containing no more than 6.4% by weight of a less bioavailable impurity, preferably no more than 5.6% by weight of a less bioavailable impurity, more preferably no more than 4.8% by weight of a less bioavailable impurity, and even more preferably no more than 4.1% by weight of a less bioavailable impurity, relative to the original amount of the orally active nucleotide analogue or the orally active nucleotide analogue prodrug, when the unit dose of the composition containing 10 mg of said nucleotide analogue or nucleotide analogue prodrug is being dissolved in 500 milliliters of purified water maintained at 37° C. and stirred at 50 rpm by a dissolution paddle for a period of 2 hours.

In a further embodiment, the invention provides a composition comprising an orally active nucleotide analogue or an orally active nucleotide analogue prodrug, which is orally bioavailable, and a pharmaceutically acceptable and inactive polymer that stabilizes said nucleotide analogue or nucleotide analogue prodrug against degradation, wherein the orally active nucleotide analogue or orally active nucleotide analogue prodrug degrades to provide a solution containing no more than 4.2% by weight of a less bioavailable impurity, preferably no more than 3.6% by weight of a less bioavailable impurity, more preferably no more than 3.0% by weight of a less bioavailable impurity, and even more preferably no more than 2.5% by weight of a less bioavailable impurity, relative to the original amount of the orally active nucleotide analogue or the orally active nucleotide analogue prodrug, when the unit dose of the composition containing 10 mg of said nucleotide analogue or nucleotide analogue prodrug is being dissolved in 500 milliliters of purified water maintained at 37° C. and stirred at 50 rpm by a dissolution paddle for a period of 1 hour.

In a further embodiment, the invention provides a composition comprising an orally active nucleotide analogue or an orally active nucleotide analogue prodrug, which is orally bioavailable, and a pharmaceutically acceptable and inactive polymer that stabilizes said nucleotide analogue or nucleotide analogue prodrug against degradation, wherein the orally active nucleotide analogue or orally active nucleotide analogue prodrug degrades to provide a solution containing no more than 3.0% by weight of a less bioavailable impurity, preferably no more than 2.5% by weight of a less bioavailable impurity, more preferably no more than 2.0% by weight of a less bioavailable impurity, and even more preferably no more than 1.5% by weight of a less bioavailable impurity, relative to the original amount of the orally active nucleotide analogue or the orally active nucleotide analogue prodrug, when the unit dose of the composition containing 10 mg of said nucleotide analogue or nucleotide analogue prodrug is being dissolved in 500 milliliters of purified water maintained at 37° C. and stirred at 50 rpm by a dissolution paddle for a period of 30 minutes.

The invention further provides a container/closure package system containing a composition in accordance with any of the embodiments above, accompanied by printed materials informing a patient or a medical care worker that the orally active nucleotide analogue or the orally active nucleotide analogue prodrug of such composition has been formulated to possess high purity and resistance to destabilization by decomposing or degrading to provide a composition containing no more than 1.5% by weight of a less orally bioavailable impurity, preferably no more than 1.2% by weight of a less orally bioavailable impurity, and/or more preferably no more than 1.0% by weight of a less orally bioavailable impurity, of the orally active nucleotide analogue or of the orally active nucleotide analogue prodrug, for the shelf-life of the composition contained in the container/closure package system.

In accordance with an embodiment, the invention provides a container/closure package system containing a composition as described above and printed materials informing a patient or a medical care worker that the orally active nucleotide analogue or the orally active nucleotide analogue prodrug of the composition has been formulated to possess high purity and exceptional resistance to aqueous solution degradation by decomposing to no more than 10.0%, preferably no more than 5.0%, and more preferably no more than 2.0% by weight of the less orally bioavailable impurity of the orally active nucleotide analogue or the orally active nucleotide analogue prodrug, relative to the original amount of the orally active nucleotide analogue or the orally active nucleotide analogue prodrug, when it is dissolved in the gastrointestinal fluids and/or when it is absorbed in the blood before reaching its target cells in the body, for the shelf-life of the composition contained in the container/closure package system.

In an embodiment, the container/closure package system includes printed materials which further inform a patient or a medical care worker that the high purity and resistance to degradation, including the exceptional aqueous solution degradation, of the orally active nucleotide analogue or the orally active nucleotide analogue prodrug contained in the composition are required to reach the fullest therapeutic effect and achieve the best therapeutic mode intended for the composition of said orally active nucleotide analogue or the orally active nucleotide analogue prodrug.

In an embodiment, the container/closure package system of the invention includes printed materials which further inform a patient or a medical care worker that the high purity and resistance to degradation, including the exceptional aqueous solution degradation, of the contained composition of the orally active nucleotide analogue or the orally active nucleotide analogue prodrug are required to achieve the optimum safety and efficacy levels intended for the composition.

The invention further provides a container/closure package system containing a composition in accordance with any of the embodiments above, accompanied by printed materials informing a patient or a medical care worker that the orally active nucleotide analogue or the orally active nucleotide analogue prodrug of such composition has been formulated to possess exceptional resistance to in-situ aqueous solution degradation, since it degrades minimally to its less orally bioavailable impurities when such nucleotide analogue or nucleotide analogue prodrug dissolves in the gastrointestinal fluids from the composition contained in the container/closure package system and gets absorbed in the blood.

The printed materials accompanying the container/closure package system can also inform a patient or a medical care worker that the high purity and resistance to destabilization during storage, and/or the exceptional resistance to in-situ aqueous solution degradation of the orally active nucleotide analogue or the orally active nucleotide analogue prodrug contained in the packaged composition are required to reach the fullest therapeutic effect and achieve the best therapeutic mode intended for the composition of said nucleotide analogue or said nucleotide analogue prodrug. In an embodiment, the printed materials accompanying the container/closure package system also inform a patient or a medical care worker that the high purity and resistance to destabilization during storage, and/or the exceptional resistance to in-situ aqueous solution degradation of the contained composition of the nucleotide analogue or the nucleotide analogue prodrug are required to achieve the optimum safety and efficacy levels intended for the composition.

The present invention further provides a liquid solution comprising an orally active nucleotide analogue or an orally active nucleotide analogue prodrug described above, a pharmaceutically acceptable inactive polymer, and an organic solvent, wherein the nucleotide analogue or the nucleotide analogue prodrug is stable to degradation to form a less bioavailable impurity in the liquid solution.

In an embodiment, the invention provides a liquid solution comprising an orally active nucleotide analogue or an orally active nucleotide analogue prodrug, a pharmaceutically acceptable inactive polymer, and a liquid organic solvent, wherein the orally active nucleotide analogue or the orally active nucleotide analogue prodrug is stable to degradation to form a less bioavailable impurity in said liquid solution; wherein said less bioavailable impurity has at least 10% less oral bioavailability than the orally active nucleotide analogue or the orally active nucleotide analogue prodrug.

For example, the phosphonate nucleotide analogue prodrug is 9-[2-[bis[(pivaloyloxy)-methoxy]phosphinyl]methoxy]ethyl]adenine (the bis(POM)PMEA diester of adefovir) or 9-[(R)-2-[bis[(isopropoxycarbonyl)oxymethoxy]-phosphinyl]methoxy]propyl]adenine (the bis(POC)PMPA diester of tenofovir). In an embodiment, the less orally bioavailable impurity includes 9-[2-(pivaloyloxy)-methoxyphosphinyl]methoxy]ethyl]adenine, 9-[(R)-2-[(isopropoxycarbonyl)oxy]-methoxyphosphinyl]methoxy]propyl]adenine, adefovir, and/or tenofovir.

In an embodiment, the polymer present in the liquid solution is copovidone, a vinylpyrrolidone-vinyl acetate copolymer.

In accordance with the invention, the liquid solution can include any suitable organic solvent, for example, a volatile organic solvent, or a mixture of volatile organic solvents, that has a boiling point below 100° C. at a pressure of 1 atmosphere and is selected from the group consisting of volatile alcohols, volatile ketones and volatile halocarbons and combinations thereof, in which the nucleotide analogue or the nucleotide analogue prodrug is stable. In an embodiment, the organic solvent is acetone.

In accordance with the invention, the composition comprising the orally active nucleotide analogue or the orally active nucleotide analogue prodrug can be prepared by rapidly evaporating the solvent from a liquid solution as described above, e.g., at a rate of about 30% to about 50% or more of the solvent per hour.

The invention provides, in an embodiment, a composition comprising a dried mass obtained by rapidly evaporating the solvent from the liquid solution as described above, wherein the orally active nucleotide analogue or the orally active nucleotide analogue prodrug is stable in the dried mass. In an embodiment, the dried mass is a stable amorphous solid solution of the nucleotide analogue or the nucleotide analogue prodrug and the polymer. In a particular embodiment, the amorphous solid solution of the orally active nucleotide analogue prodrug and the polymer is a molecular dispersion of adefovir dipivoxil or tenofovir disoproxil and copovidone.

The composition comprising a dried mass as described above may further include one or more pharmaceutically acceptable inactive ingredients, for example, one or more pharmaceutically acceptable inactive ingredients are selected from the group consisting of fillers, diluents, binders, disintegrants, glidants, lubricants and matrix forming materials. Thus, for example, the one or more pharmaceutically acceptable inactive ingredients are selected from the group consisting of anhydrous lactose, microcrystalline cellulose, silicon dioxide, and magnesium stearate. The composition comprising a dried mass as described above can be in any solid dosage form, e.g., a tablet, a capsule, or a powder.

The present invention further provides a method of manufacturing a form or a composition of an orally active nucleotide analogue or an orally active nucleotide analogue prodrug as described above, comprising combining an orally active nucleotide analogue or an orally active nucleotide analogue prodrug with a polymer that stabilizes the nucleotide analogue or the nucleotide analogue prodrug against degradation to a less orally bioavailable impurity when such stabilized form or composition of said orally active nucleotide analogue or nucleotide analogue prodrug is stored, or suspended or dissolved in aqueous environments.

The present invention further provides a method of manufacturing a container/closure package system as described above, comprising providing a composition containing an orally active nucleotide analogue or an orally active nucleotide analogue prodrug wherein the nucleotide analogue or the nucleotide analogue prodrug is stable during storage and/or during dissolution in aqueous environments against degradation to a less orally bioavailable impurity and providing the printed materials in combination therewith.

The present invention further provides a method of manufacturing a liquid solution of an orally active nucleotide analogue or an orally active nucleotide analogue prodrug as described above comprising combining the nucleotide analogue or the nucleotide analogue prodrug and a volatile organic solvent.

The present invention further provides a method of treating a patient for a disease or condition treatable by an orally active nucleotide or an orally active nucleotide analogue prodrug comprising administering to the patient an effective amount of a composition as described above. The present invention further provides a method of treating a patient for a disease or condition treatable by an orally active nucleotide analogue or an orally active nucleotide analogue prodrug comprising administering to the patient an effective amount of a composition comprising the nucleotide analogue or the nucleotide analogue prodrug taken from a container/closure package system as described above.

The following examples further illustrate the invention but, of course, should not be construed as in any way limiting its scope.

Example 1

This example demonstrates a method of preparing and characterizing a composition in accordance with an embodiment of the invention.

The orally active nucleotide analogue prodrug, AD, was dissolved in acetone along with copovidone (Polyplasdone S-630), a vinylpyrrolidone-vinyl acetate copolymer. The solution was then placed in trays and dried rapidly in a vacuum oven operating at low temperature (i.e., at no more than 35-40° C.) and at pressures close to 0 atm. After 2-3 hours of such vacuum drying, the resulting dried film was removed from the trays milled to a fine powder and re-dried in a regular convection oven for another 4-6 hours at low temperature (i.e., at not more than 35-40° C.) to remove any residual acetone.

The resulting dried AD/polymer powder is an amorphous, 11.6% w/w solid solution of AD molecules dissolved in the copovidone polymer molecules. X-Ray Diffraction studies conducted on the AD/polymer powder after storage at several temperature and humidity conditions, verified that the prepared AD/polymer solid solution is indeed amorphous since no diffraction 2-theta peaks were observed in the diffractograms of this material and, also, no such peaks were observed similar to those described and depicted as characteristic diffraction 2-theta peaks in the diffractograms of crystalline AD forms claimed by Arimilli et al. in U.S. Pat. No. 6,451,340.

The amorphous AD/polymer powder was subsequently dry-mixed with other pharmaceutically acceptable inactive ingredients such as the diluents anhydrous lactose and microcrystalline cellulose, the disintegrant crospovidone, the glidant amorphous silicon dioxide, and the lubricant magnesium stearate, to produce a pharmaceutical formulation in quantities equivalent to about 50,000 tablets (i.e., SP-Lot #PD0023:11) and 200,000 units (i.e., SP-Lot #BB0030023), each of these tablets containing 10 mg of AD.

Example 2

This example demonstrates the storage stability of the composition prepared in accordance with an embodiment of the invention described in EXAMPLE 1.

Tablets from both lots prepared in EXAMPLE 1 were placed in a 30-tablet-fill configuration 60 cc HDPE plastic bottle with a 3-gram Tri-Sorb adsorbent canister system, sealed using a heat-induction membrane seal and capped by an HDPE plastic cap. They were stored along with 30-fill bottles of the brand product HEPSERA® 10-mg tablets (Lot #TGL024A), under two accelerated storage conditions, namely, at 40° C. and 75% relative humidity ("RH") and at 60° C. and 75% RH. An additional lot of the brand HEPSERA® 10-mg tablets (Lot #TGL018A) was also stored only at 60° C. and 75% RH. Furthermore, SP-Lot #BB0030023 was also stored at controlled room temperature conditions, namely, at 25° C. and 60% RH. Samples were withdrawn and tested for their impurity content, namely, the less bioavailable monoester of AD, mono(POM)PMEA, as measured in % w/w with regards to the originally contained amount of AD in each tablet. Moreover, samples of one lot of HEPSERA® 10-mg tablets (Lot #TDJ094) stored at controlled room temperature, were also tested soon after received and at their expiration date for their mono(POM) PMEA impurity content.

A validated, stability indicating HPLC method was used for such analysis of the stability storage samples.

The accelerated storage stability results obtained are set forth in Tables 1 and 2.

TABLE 1

Comparison of Impurity Levels expressed in Weight Percent of the Monoester Impurity, mono(POM)PMEA, detected in Adefovir Dipivoxil ("AD") 10-mg Tablets made according to an embodiment of the invention and commercial HEPSERA ® Tablets 10 mg, stored at 40° C. and 75% Relative Humidity ("RH") for Three Months.

| Time of Storage at 40° C. and 75% RH of AD Tablets, 10 mg | Weight % of Impurity relative to AD | | |
|---|---|---|---|
| | SP-Lot # PD0023: 11 | SP-Lot # BB0030023 | HEPSERA ® Lot # TGL024A |
| 0 (before Storage) | 0.11% | 0.15% | 1.76% |
| 1 Month | 0.59% | 0.42% | 1.91% |
| 2 Months | 0.79% | 0.59% | 2.16% |
| 3 Months | 0.98% | 0.74% | 2.61% |

TABLE 2

Comparison of Impurity Levels expressed in Weight Percent of the Monoester Impurity, mono(POM)PMEA, detected in Adefovir Dipivoxil ("AD") 10-mg Tablets made according to an embodiment of the invention and commercial HEPSERA ® Tablets 10 mg, stored at 60° C. and 75% Relative Humidity ("RH") for Five Days.

| Time of Storage at 60° C. and 75% RH of AD Tablets, 10 mg | Weight % of Impurity relative to AD | | | |
|---|---|---|---|---|
| | SP-Lot # PD0023: 11 | SP-Lot # BB0030023 | HEPSERA ® Lot # TGL018A | HEPSERA ® Lot # TGL024A |
| 0 (before Storage) | 0.11% | 0.15% | 2.08% | 1.76% |
| 5 Days | 0.63% | 0.56% | 3.09% | 3.18% |

The data set forth in Tables 1 and 2 show that the invention yields pharmaceutical products containing orally active nucleotide analogues such as the prodrug AD, which, when stored in solid state at accelerated stability conditions, possess significantly enhanced stability properties as compared to already commercialized products such as the HEPSERA® (adefovir dipivoxil) Tablets, 10 mg marketed by Gilead Sciences, Inc. As shown above, embodiments of the invention enable one to manufacture highly stable pharmaceutical products of AD which, when placed along with one 3-gram TRI-SORB™ adsorbent canister system in a 30-fill configuration 60 cc HDPE plastic bottle, sealed with a heat induction membrane seal and capped with an HDPE plastic cap, present one or more of the following stability properties:

(a) stored for three (3) months at 40° C. and 75% RH decompose to provide a composition containing not more than 2.0% w/w, preferably 1.5% w/w, more preferably 1.0% w/w, and even more preferably not more than 0.75% w/w of their less orally bioavailable monoester of adefovir, namely, mono-(POM)PMEA, relative to the originally contained amount of AD in each unit dose of the initial product;

(b) stored for two (2) months at 40° C. and 75% RH decompose to provide a composition containing not more than 1.75% w/w, preferably 1.5% w/w, more preferably 1.0% w/w, and even more preferably not more than 0.6% w/w of their less orally bioavailable monoester of adefovir, namely, mono-(POM)PMEA, relative to the originally contained amount of AD in each unit dose of the initial product;

(c) stored for one (1) month at 40° C. and 75% RH decompose to provide a composition containing not more than 1.5% w/w, preferably 1.0% w/w, more preferably 0.75% w/w and most preferably not more than 0.5% w/w of their less orally bioavailable monoester of adefovir, namely, mono(POM)-PMEA, relative to the originally contained amount of AD in each unit dose of the initial product; or (d) stored for five (5) days at 60° C. and 75% RH decompose to provide a composition containing not more than 2.5% w/w, preferably 2.0% w/w, more preferably 1.5% w/w, most preferably 1.0% w/w and even most preferably not more than 0.7% w/w of their less orally bioavailable monoester of adefovir, namely, mono(POM)PMEA, relative to the originally contained amount of AD in each unit dose of the initial product.

The above data also show that the initial drug purity of this invention's preferred forms, compositions and pharmaceutical products of nucleotide analogue prodrugs such as AD is significantly and substantially higher than that of any other forms, compositions or pharmaceutical products of nucleotide analogues reported in the literature or actually already marketed. For example, as shown in Tables 1 and 2 above, preferred embodiments of the invention exhibited initially (at time 0) impurity levels not more than 0.2% w/w of the less bioavailable monoester of adefovir, mono(POM)PMEA. On the other hand, it could be projected from the stability results in Tables 1 and 2 above that the initial impurity levels of mono(POM)PMEA present in freshly manufactured HEPSERA® tablets are not lower than 1.0% w/w to 1.2% w/w, which is consistent with the work of Munger, Jr., et al. in U.S. Pat. No. 5,935,946, wherein it is reported that up to 1.0% w/w of the less bioavailable monoester of tenofovir, mono(POC)PMPA, had been already formed soon after production of tenofovir disoproxil fumarate, another orally active nucleotide analogue prodrug.

The foregoing observations are also in agreement with the results obtained from samples stored at controlled room temperature conditions, which are set forth in Table 3 below.

TABLE 3

Impurity Levels expressed in Weight Percent of the Monoester Impurity, mono(POM)PMEA, detected (or projected) in Adefovir Dipivoxil ("AD") 10-mg Tablets made according to an embodiment of the invention stored at controlled room temperature conditions, i.e., 25° C. and 60% Relative Humidity ("RH").

| Time of Storage at 25° C. and 60% RH of AD Tablets, 10 mg | Weight % of Impurity relative to AD | |
|---|---|---|
| | SP-Lot # BB0030023 | HEPSERA® Lot # TDJ094 |
| Time 0 (tested soon after manufacturing) | 0.15% | |
| 3 Months | 0.30% | 1.12% |
| 6 Months | 0.38% | |
| 9 Months | 0.44% | |
| 12 Months | 0.51% | |
| 18 Months | 0.65% | |
| 24 Months | | 1.65% |

As shown in Table 3, the invention yields pharmaceutical products containing orally active nucleotide analogues such as the prodrug AD, which, when stored at controlled room temperature stability conditions, possess enhanced stability properties as compared to already commercialized products such as the HEPSERA® (adefovir dipivoxil) Tablets, 10 mg marketed by Gilead Sciences, Inc. As shown above, embodiments of the invention enable one to manufacture highly stable pharmaceutical products containing AD which when placed along with one 3-gram TRI-SORB™ adsorbent canister system in a 30-fill configuration 60 cc HDPE plastic bottle, sealed with a heat induction membrane seal, and capped with an HDPE plastic cap, demonstrate one or more of the following stability properties:

(a) when stored for twenty four (24) months at 25° C. and 60% RH, they are projected to decompose or degrade to provide a composition containing not more than 1.5% w/w, preferably 1.2% w/w, more preferably 1.0% w/w, and even more preferably not more than 0.8% w/w of their less orally bioavailable monoester of adefovir, namely, mono-(POM) PMEA, relative to the originally contained amount of AD in each unit dose of the initial product; or (b) when stored for twelve (12) months at 25° C. and 60% RH, they decompose or degrade to provide a composition containing not more than 1.2% w/w, preferably 1.0% w/w, more preferably 0.8% w/w, and even more preferably not more than 0.6% w/w of their less orally bioavailable monoester of adefovir, namely, mono-(POM)PMEA, relative to the originally contained amount of AD in each unit dose of the initial product.

Furthermore, as also shown in Table 3, freshly manufactured products of AD made according to one embodiment of the invention and tested no later than about one month after their manufacturing, contain no more than 0.8% w/w, preferably 0.6% w/w, more preferably 0.4% w/w, and even more preferably no more than 0.2% w/w of their less orally bioavailable monoester of adefovir, namely, mono-(POM) PMEA, with regards to the originally contained amount of AD in each unit dose of the initial product.

Therefore, an important advantage of compositions of the invention is that they contain an amount of orally active prodrug of a nucleotide analogue which is much closer to the label amount of the contained prodrug, initially and substantially for the shelf-life of the compositions. Hence, it is possible for new label claims to be included in container/closure package systems of a composition of the present invention wherein patients and medical care workers are informed that the contained composition of the orally active nucleotide analogues or the orally active nucleotide analogue prodrugs have exceptional purity and resistance to destabilization since they degrade to provide a composition having no more than 1.5% w/w, preferably 1.2%, more preferably 1.0% w/w, and even more preferably no more than 0.8% w/w of their less bioavailable impurities for the shelf-life of the composition, and that such high purity and resistance to destabilization are required to achieve the best therapeutic mode, including optimum safety and efficacy, intended for such packaged pharmaceutical compositions of the orally active nucleotide analogues or the orally active nucleotide analogue prodrugs.

Example 3

This example demonstrates the resistance to drug degradation during dissolution in an aqueous environment of the composition prepared in accordance with an embodiment of the invention described in EXAMPLE 1.

Three tablets of SP-Lot #BB0030023, each containing 10 mg of AD and prepared as described in EXAMPLE 1, and three tablets of HEPSERA® 10-mg tablets (Lot #TDJ094), were each placed in a 500 mL glass beaker containing 250 mL of purified water maintained at 37° C. and agitated with a magnetic stirrer revolving at 60 rpm. Similarly, three 10-mg AD tablets of SP-Lot #BB0030023 and three tablets of HEPSERA® 10-mg tablets (Lot # TDJ094), were each placed in a 1000 mL glass dissolution vessel containing 500 mL of purified water maintained at 37° C. and agitated with a dissolution paddle operating at 50 rpm. Dissolution samples were withdrawn and tested for their impurity content, namely, the less bioavailable monoester of AD, mono(POM)PMEA, which was then extrapolated to obtain the % w/w of mono(POM)PMEA relative to the originally contained amount of AD in each tablet (i.e., 10 mg of AD).

A validated, stability indicating HPLC method was used to analyze the dissolution samples obtained above.

The aqueous solution stability results obtained are tabulated in Tables 4 and 5.

TABLE 4

Comparison of Impurity Levels expressed in Weight Percent of the Monoester Impurity, mono(POM)PMEA, detected in dissolution samples when Adefovir Dipivoxil ("AD") 10-mg Tablets made according to an embodiment of the invention and commercial HEPSERA ® Tablets 10 mg, were dissolved in 250 mL of purified water maintained at 37° C. and agitated at 60 rpm by a magnetic stirrer.

| Time of Dissolution of AD | Weight % of Impurity relative to AD | |
| --- | --- | --- |
| Tablets, 10 mg in 250 mL of Purified Water | SP-Lot # BB0030023 | HEPSERA ® Lot # TDJ094 |
| 0.5 h | 2.05% | 7.42% |
| 1 h | 3.01% | 11.61% |

TABLE 5

Comparison of Impurity Levels expressed in Weight Percent of the Monoester Impurity, mono(POM)PMEA, detected in dissolution samples when Adefovir Dipivoxil ("AD") 10-mg Tablets made according to an embodiment of the invention and commercial HEPSERA ® Tablets 10 mg, were dissolved in 500 mL of purified water maintained at 37° C. and agitated at 50 rpm by a dissolution paddle.

| Time of Dissolution of AD | Weight % of Impurity relative to AD | |
| --- | --- | --- |
| Tablets, 10 mg in 500 mL of Purified Water | SP-Lot # BB0030023 | HEPSERA ® Lot # TDJ094 |
| 0.5 h | 1.12% | 3.30% |
| 1 h | 2.07% | 4.66% |
| 2 h | 3.66% | 7.15% |

As shown in Tables 4 and 5, the invention provides pharmaceutical products of orally active nucleotide analogues such as the prodrug AD, which, when dissolved in aqueous environments, demonstrate surprisingly better resistance to aqueous solution degradation of AD to its less bioavailable monoester impurity as compared to already commercialized products such as the HEPSERA® (adefovir dipivoxil) Tablets, 10 mg marketed by Gilead Sciences, Inc. As shown above, embodiments of the invention enable one to manufacture a highly stable 10-mg tablet of AD which, when dissolved in 250 mL of purified water maintained at 37° C. and stirred at 60 rpm, displays exceptional resistance to degradation in the aqueous solution by forming a dissolved composition wherein:

(a) after one (1) hour of dissolution, no more than 10.5% w/w, preferably no more than 8.5% w/w, more preferably no more than 6.0% w/w, and even more preferably no more than 4.0% w/w of its less orally bioavailable monoester of adefovir, relative to the originally contained amount of AD in each tablet; and/or (b) after thirty (30) minutes of dissolution, no more than 6.5% w/w, preferably no more than 5.5% w/w, more preferably no more than 4.3% w/w, and even more preferably no more than 3.0% w/w of its less orally bioavailable monoester of adefovir, relative to the originally contained amount of AD in each tablet.

Furthermore, as also shown above, embodiments of the invention enable one to manufacture a highly stable 10-mg tablet of AD which, when dissolved in 500 mL of purified water maintained at 37° C. and agitated at a paddle speed of 50 rpm, demonstrates exceptional resistance to degradation in the aqueous solution by forming a dissolved composition wherein:

(a) after two (2) hours of dissolution, no more than 6.4% w/w, preferably no more than 5.6% w/w, more preferably no more than 4.8% w/w, and even more preferably no more than 4.1% w/w of its less orally bioavailable monoester of adefovir, relative to the originally contained amount of AD in each tablet;

(b) after one (1) hour of dissolution, no more than 4.2% w/w, preferably no more than 3.6% w/w, more preferably no more than 3.0% w/w, and even more preferably no more than 2.5% w/w of its less orally bioavailable monoester of adefovir, relative to the originally contained amount of AD in each tablet; and/or (c) after thirty (30) minutes of dissolution, no more than 3.0% w/w, preferably no more than 2.5% w/w, more preferably no more than 2.0% w/w, and even more preferably no more than 1.5% w/w of its less orally bioavailable monoester of adefovir, relative to the originally contained amount of AD in each tablet.

Therefore, another important and surprising advantage of compositions of the invention is that they can demonstrate exceptional resistance to degradation, e.g., in-situ degradation, when dissolved in aqueous environments such as blood and gastrointestinal fluids. Such resistance of the compositions to aqueous solution degradation of their orally active nucleotide analogue prodrug (e.g., AD), is two to four times better than the same resistance to aqueous solution degradation of already existing and commercialized dosage forms of AD. Such vast improvement of the resistance to aqueous solution degradation of orally active nucleotide analogues and nucleotide analogue prodrugs leads to new and improved commercial compositions of such compounds made in accordance to this invention, which would not only be more efficacious than older forms, compositions or existing commercial products of said compounds, but also, would permit reduction of the required therapeutic dose regimen of such orally active nucleotide analogues and orally active nucleotide analogue prodrugs, thereby also increasing the safety profiles of said new and improved compositions of the invention.

Furthermore, based on the foregoing, it is also possible for new label claims to be included in container/closure package systems of this invention's products wherein patients and medical care workers are informed that: (a) the products containing orally active nucleotide analogues or orally active nucleotide analogue prodrugs have exceptional purity, storage stability properties and/or resistance to in-situ degradation in aqueous environments such as blood and gastrointestinal fluids; (b) compared to older products, the products of the present invention decompose or degrade very minimally to their less orally bioavailable impurities when they are manufactured, stored and/or dissolved in said aqueous environments for the shelf-life of the contained products; and (c) such high purity, storage stability properties and resistance to in-situ aqueous solution degradation are desirable to achieve the best therapeutic mode, including optimum safety and efficacy of such packaged pharmaceutical products of the orally active nucleotide analogues or the orally active nucleotide analogue prodrugs.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition comprising an orally active nucleotide analogue phosphonate prodrug which is amorphous, which is orally bioavailable, and a pharmaceutically acceptable and inactive polymer that stabilizes the orally active nucleotide analogue phosphonate prodrug against degradation, wherein the nucleotide analogue phosphonate prodrug degrades to provide a composition containing no more than (a) 0.8% by weight of a less bioavailable impurity, relative to the original amount of the orally active nucleotide analogue phosphonate prodrug, when the composition is maintained at a temperature of 25° C. and at a relative humidity (RH) of 60% for a period of 1 month; (b) 1.2% by weight of a less bioavailable impurity, relative to the original amount of the orally active nucleotide analogue phosphonate prodrug, when the composition is maintained at a temperature of 25° C. and at 60% RH for a period of 12 months; (c) 1.5% by weight of a less bioavailable impurity, relative to the original amount of the orally active nucleotide analogue phosphonate prodrug, when the composition is maintained at a temperature of 25° C. and at 60% RH for a period of 24 months; (d) 2.0% by weight of a less bioavailable impurity, relative to the original amount of the orally active nucleotide analogue phosphonate prodrug, when the composition is maintained at a temperature of 40° C. and at 75% RH for a period of 3 months; (e) 1.75% by weight of a less bioavailable impurity, relative to the original amount of the orally active nucleotide analogue phosphonate prodrug, when the composition is maintained at a temperature of 40° C. and at 75% RH for a period of 2 months; (f) 1.5% by weight of a less bioavailable impurity, relative to the original amount of the orally active nucleotide analogue phosphonate prodrug, when the composition is maintained at a temperature of 40° C. and at 75% RH for a period of 1 month; and/or (g) 2.5% by weight of a less bioavailable impurity, relative to the original amount of the orally active nucleotide analogue prodrug, when the composition is maintained at a temperature of 60° C. and at 75% RH for a period of 5 days; wherein said less bioavailable impurity has at least 10% less oral bioavailability than the orally active nucleotide analogue phosphonate prodrug;
   wherein the nucleotide analogue phosphonate prodrug is 9-[2-[bis[(pivaloyloxy)-methoxy]phosphinyl]methoxy]ethyl]adenine (or bis(POM)PMEA diester of adefovir) or 9-[(R)-2-[bis[(isopropoxycarbonyl)oxymethoxy]-phosphinyl]methoxy]propyl]adenine (or bis(POC)PMPA diester of tenofovir);
   wherein the less orally bioavailable impurity is 9-[2-(pivaloyloxy)-methoxyphosphinyl]methoxy]ethyl]adenine, 9-[(R)-2-[(isopropoxycarbonyl)oxy]methoxyphosphinyl]methoxy]propyl]adenine, adefovir, tenofovir, or any combination thereof; and wherein the composition is an amorphous solid solution of the nucleotide analogue phosphonate prodrug and the pharmaceutically acceptable inactive polymer wherein the amorphous solid solution of the orally active nucleotide analogue phosphonate prodrug and the pharmaceutically acceptable inactive polymer is produced by dissolving the orally active nucleotide analogue phosphonate prodrug and the pharmaceutically acceptable inactive polymer in a liquid organic solvent and evaporating the organic solvent.

2. The composition of claim 1, wherein the nucleotide analogue phosphonate prodrug is 9-[2-[bis[(pivaloyloxy)-methoxy]phosphinyl]methoxy]ethyl]adenine (or bis(POM) PMEA diester of adefovir).

3. The composition of claim 1, further including one or more pharmaceutically acceptable inactive ingredients.

4. The composition of claim 3, wherein the one or more pharmaceutically acceptable inactive ingredients are selected from the group consisting of fillers, diluents, binders, disintegrants, glidants, lubricants, and matrix forming materials.

5. The composition of claim 3, wherein the one or more pharmaceutically acceptable inactive ingredients are selected from the group consisting of anhydrous lactose, microcrystalline cellulose, silicon dioxide, and magnesium stearate.

6. The composition of claim 3, wherein the composition is a solid dosage form.

7. The composition of claim 6, wherein the solid dosage form is a tablet, a capsule, or a powder.

8. The composition of claim 1, wherein the liquid organic solvent is selected from the group consisting of volatile alcohols, volatile ketones, and volatile halocarbons, and combinations thereof.

9. The composition of claim 8, wherein the orally active nucleotide analogue phosphonate prodrug is adefovir dipivoxil and the liquid organic solvent is acetone.

10. The composition of claim 9, wherein the orally active nucleotide analogue prodrug degrades to provide a composition containing no more than 0.6% by weight of the less bioavailable impurity, relative to the original amount of the orally active nucleotide analogue prodrug, when the composition is maintained at a temperature of 25° C. and at 60% RH for a period of 1 month.

11. The composition of claim 10, wherein the orally active nucleotide analogue prodrug degrades to provide a composition containing no more than 0.4% by weight of the less bioavailable impurity, relative to the original amount of the orally active nucleotide analogue prodrug, when the composition is maintained at a temperature of 25° C. and at 60% RH for a period of 1 month.

12. The composition of claim 11, wherein the orally active nucleotide analogue prodrug degrades to provide a composition containing no more than 0.2% by weight of the less bioavailable impurity, relative to the original amount of the orally active nucleotide analogue prodrug, when the composition is maintained at a temperature of 25° C. and at 60% RH for a period of 1 month.

13. The composition of claim 1, wherein the orally active nucleotide analogue or the orally active nucleotide analogue prodrug degrades to provide a composition containing no more than 1.0% by weight of the less bioavailable impurity, relative to the original amount of the orally active nucleotide analogue or the orally active nucleotide analogue prodrug, when the composition is maintained at a temperature of 25° C. and at 60% RH for a period of 12 months.

14. The composition of claim 9, wherein the orally active nucleotide analogue prodrug degrades to provide a composition containing no more than 0.8% by weight of the less bioavailable impurity, relative to the original amount of the orally active nucleotide analogue prodrug, when the composition is maintained at a temperature of 25° C. and at 60% RH for a period of 12 months.

15. The composition of claim 14, wherein the orally active nucleotide analogue prodrug degrades to provide a composition containing no more than 0.6% by weight of the less bioavailable impurity, relative to the original amount of the orally active nucleotide analogue prodrug, when the composition is maintained at a temperature of 25° C. and at 60% RH for a period of 12 months.

16. The composition of claim 1, wherein the orally active nucleotide analogue or the orally active nucleotide analogue prodrug degrades to provide a composition containing no more than 1.2% by weight of the less bioavailable impurity, relative to the original amount of the orally active nucleotide analogue or the orally active nucleotide analogue prodrug, when the composition is maintained at a temperature of 25° C. and at 60% RH for a period of 24 months.

17. The composition of claim 1, wherein the orally active nucleotide analogue or the orally active nucleotide analogue prodrug degrades to provide a composition containing no more than 1.0% by weight of the less bioavailable impurity, relative to the original amount of the orally active nucleotide analogue or the orally active nucleotide analogue prodrug, when the composition is maintained at a temperature of 25° C. and at 60% RH for a period of 24 months.

18. The composition of claim 9, wherein the orally active nucleotide analogue prodrug degrades to provide a composition containing no more than 0.8% by weight of the less bioavailable impurity, relative to the original amount of the orally active nucleotide analogue prodrug, when the composition is maintained at a temperature of 25° C. and at 60% RH for a period of 24 months.

19. The composition of claim 1, wherein the orally active nucleotide analogue or the orally active nucleotide analogue prodrug degrades to provide a composition containing no more than 1.5% by weight of the less bioavailable impurity, relative to the original amount of the orally active nucleotide analogue or the orally active nucleotide analogue prodrug, when the composition is maintained at a temperature of 40° C. and at 75% RH for a period of 3 months.

20. The composition of claim 1, wherein the orally active nucleotide analogue or the orally active nucleotide analogue prodrug degrades to provide a composition containing no more than 1.0% by weight of the less bioavailable impurity, relative to the original amount of the orally active nucleotide analogue or the orally active nucleotide analogue prodrug, when the composition is maintained at a temperature of 40° C. and at 75% RH for a period of 3 months.

21. The composition of claim 9, wherein the orally active nucleotide analogue prodrug degrades to provide a composition containing no more than 0.75% by weight of the less bioavailable impurity, relative to the original amount of the orally active nucleotide analogue prodrug, when the composition is maintained at a temperature of 40° C. and at 75% RH for a period of 3 months.

22. The composition of claim 1, wherein the orally active nucleotide analogue or the orally active nucleotide analogue prodrug degrades to provide a composition containing no more than 1.5% by weight of the less bioavailable impurity, relative to the original amount of the orally active nucleotide analogue or the orally active nucleotide analogue prodrug, when the composition is maintained at a temperature of 40° C. and at 75% RH for a period of 2 months.

23. The composition of claim 1, wherein the orally active nucleotide analogue or the orally active nucleotide analogue prodrug degrades to provide a composition containing no more than 1.0% by weight of the less bioavailable impurity, relative to the original amount of the orally active nucleotide analogue or the orally active nucleotide analogue prodrug, when the composition is maintained at a temperature of 40° C. and at 75% RH for a period of 2 months.

24. The composition of claim 9, wherein the orally active nucleotide analogue prodrug degrades to provide a composition containing no more than 0.6% by weight of the less bioavailable impurity, relative to the original amount of the orally active nucleotide analogue prodrug, when the composition is maintained at a temperature of 40° C. and at 75% RH for a period of 2 months.

25. The composition of claim 9, wherein the orally active nucleotide analogue phosphonate prodrug degrades to provide a composition containing no more than 1.0% by weight of the less bioavailable impurity, relative to the original amount of the orally active nucleotide analogue phosphonate prodrug, when the composition is maintained at a temperature of 40° C. and at 75% RH for a period of 1 month.

26. The composition of claim 9, wherein the orally active nucleotide analogue phosphonate prodrug degrades to provide a composition containing no more than 0.75% by weight of the less bioavailable impurity, relative to the original amount of the orally active nucleotide analogue phosphonate prodrug, when the composition is maintained at a temperature of 40° C. and at 75% RH for a period of 1 month.

27. The composition of claim 9, wherein the orally active nucleotide analogue phosphonate prodrug degrades to provide a composition containing no more than 0.5% by weight of the less bioavailable impurity, relative to the original amount of the orally active nucleotide analogue phosphonate prodrug, when the composition is maintained at a temperature of 40° C. and at 75% RH for a period of 1 month.

28. The composition of claim 1, wherein the orally active nucleotide analogue or the orally active nucleotide analogue prodrug degrades to provide a composition containing no more than 2.0% by weight of the less bioavailable impurity, relative to the original amount of the orally active nucleotide analogue or the orally active nucleotide analogue prodrug, when the composition is maintained at a temperature of 60° C. and at 75% RH for a period of 5 days.

29. The composition of claim 1, wherein the orally active nucleotide analogue or the orally active nucleotide analogue prodrug degrades to provide a composition containing no more than 1.5% by weight of the less bioavailable impurity, relative to the original amount of the orally active nucleotide analogue or the orally active nucleotide analogue prodrug, when the composition is maintained at a temperature of 60° C. and at 75% RH for a period of 5 days.

30. The composition of claim 1, wherein the orally active nucleotide analogue or the orally active nucleotide analogue prodrug degrades to provide a composition containing no more than 1.0% by weight of the less bioavailable impurity, relative to the original amount of the orally active nucleotide analogue or the orally active nucleotide analogue prodrug, when the composition is maintained at a temperature of 60° C. and at 75% RH for a period of 5 days.

31. The composition of claim 9, wherein the orally active nucleotide analogue prodrug degrades to provide a composition containing no more than 0.7% by weight of the less bioavailable impurity, relative to the original amount of the orally active nucleotide analogue prodrug, when the composition is maintained at a temperature of 60° C. and at 75% RH for a period of 5 days.

32. The composition of claim 25, further including one or more pharmaceutically acceptable inactive ingredients.

33. The composition of claim 32, wherein the one or more pharmaceutically acceptable inactive ingredients are selected from the group consisting of fillers, diluents, binders, disintegrants, glidants, lubricants, and matrix forming materials.

34. The composition of claim 32, wherein the one or more pharmaceutically acceptable inactive ingredients are selected from the group consisting of anhydrous lactose, microcrystalline cellulose, silicon dioxide, and magnesium stearate.

35. The composition of claim 32, wherein the composition is a solid dosage form.

36. The composition of claim 35, wherein the solid dosage form is a tablet, a capsule, or a powder.

37. The composition of claim 26, further including one or more pharmaceutically acceptable inactive ingredients.

38. The composition of claim 37, wherein the one or more pharmaceutically acceptable inactive ingredients are selected from the group consisting of fillers, diluents, binders, disintegrants, glidants, lubricants, and matrix forming materials.

39. The composition of claim 37, wherein the one or more pharmaceutically acceptable inactive ingredients are selected from the group consisting of anhydrous lactose, microcrystalline cellulose, silicon dioxide, and magnesium stearate.

40. The composition of claim 37, wherein the composition is a solid dosage form.

41. The composition of claim 40, wherein the solid dosage form is a tablet, a capsule, or a powder.

42. The composition of claim 37, further including one or more pharmaceutically acceptable inactive ingredients.

43. The composition of claim 42, wherein the one or more pharmaceutically acceptable inactive ingredients are selected from the group consisting of fillers, diluents, binders, disintegrants, glidants, lubricants, and matrix forming materials.

44. The composition of claim 42, wherein the one or more pharmaceutically acceptable inactive ingredients are selected from the group consisting of anhydrous lactose, microcrystalline cellulose, silicon dioxide, and magnesium stearate.

45. The composition of claim 42, wherein the composition is a solid dosage form.

46. The composition of claim 45, wherein the solid dosage form is a tablet, a capsule, or a powder.

* * * * *